US007525097B2

United States Patent
Dorscheid et al.

(10) Patent No.: US 7,525,097 B2
(45) Date of Patent: Apr. 28, 2009

(54) MODULAR DEVICE FOR THE DETECTION AND/OR TRANSMISSION OF RADIATION WITH SELF-ALIGNING MODULES

(75) Inventors: Ralf Dorscheid, Kerkrade (NL); Gereon Vogtmeier, Aachen (DE); Roger Steadman, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 309 days.

(21) Appl. No.: 10/599,422

(22) PCT Filed: Mar. 22, 2005

(86) PCT No.: PCT/IB2005/050971

§ 371 (c)(1),
(2), (4) Date: Sep. 28, 2006

(87) PCT Pub. No.: WO2005/096946

PCT Pub. Date: Oct. 20, 2005

(65) Prior Publication Data

US 2008/0230706 A1  Sep. 25, 2008

(30) Foreign Application Priority Data

Apr. 6, 2004 (EP) ............................ 04101415

(51) Int. Cl.
*H01L 27/146* (2006.01)

(52) U.S. Cl. ..................... 250/370.09; 250/370.11; 378/19

(58) Field of Classification Search .................. None
See application file for complete search history.

(56) References Cited

U.S. PATENT DOCUMENTS

| 4,338,521 | A | | 7/1982 | Shaw et al. |
| 4,521,689 | A | * | 6/1985 | Pritzkow ................. 250/385.1 |
| 5,263,075 | A | | 11/1993 | McGann et al. |
| 5,487,098 | A | * | 1/1996 | Dobbs et al. .................. 378/19 |
| 5,606,589 | A | | 2/1997 | Pellegrino et al. |
| 5,991,357 | A | | 11/1999 | Marcovici et al. |
| 6,115,448 | A | | 9/2000 | Hoffman |
| 6,181,767 | B1 | | 1/2001 | Harootian |
| 6,587,538 | B2 | * | 7/2003 | Igarashi et al. ................ 378/19 |
| 6,990,176 | B2 | * | 1/2006 | Sherman et al. ............ 378/98.8 |
| 7,321,653 | B2 | * | 1/2008 | Hockersmith et al. ....... 378/144 |
| 2002/0064252 | A1 | | 5/2002 | Igarashi et al. |
| 2005/0156114 | A1 | * | 7/2005 | Yokoi et al. ............ 250/370.09 |
| 2007/0242804 | A1 | * | 10/2007 | Vogtmeier et al. .......... 378/181 |

FOREIGN PATENT DOCUMENTS

JP  2000 014665 A  1/2000

* cited by examiner

*Primary Examiner*—David P Porta
*Assistant Examiner*—Jessica L Eley

(57) ABSTRACT

The invention relates to a device for the detection and/or transmission of radiation, particularly an X-ray detector 1, that consists of a carrier 10 on which an array of detector modules 20 is arranged. The carrier 10 comprises holes 11 through which a ball at the backside of the detector modules 20 can be inserted in order to fix the modules such that they can still rotate to a certain degree. Due to this freedom, the sensor modules 20 can align themselves during assembly.

19 Claims, 1 Drawing Sheet

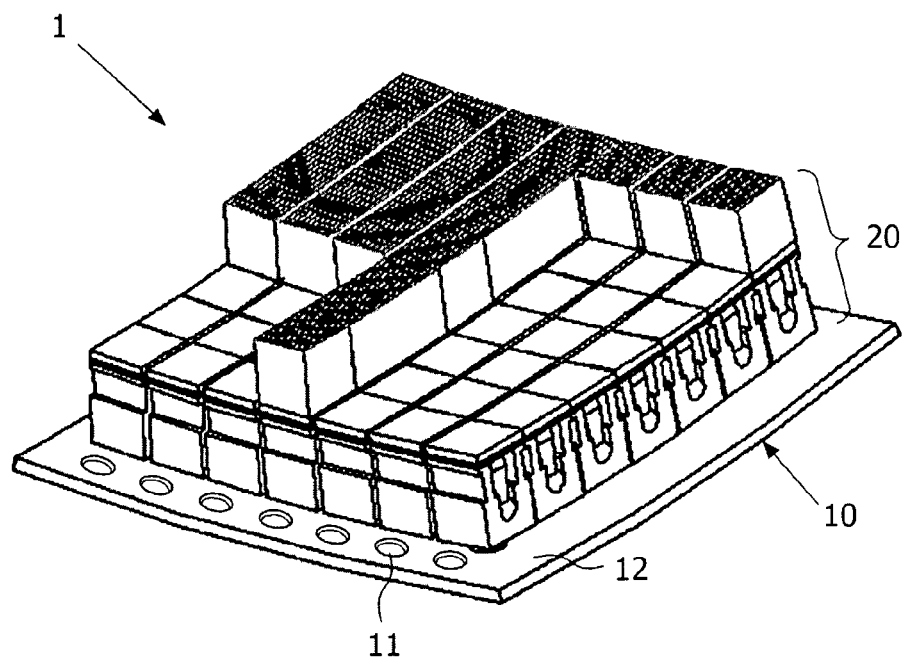
FIG.1
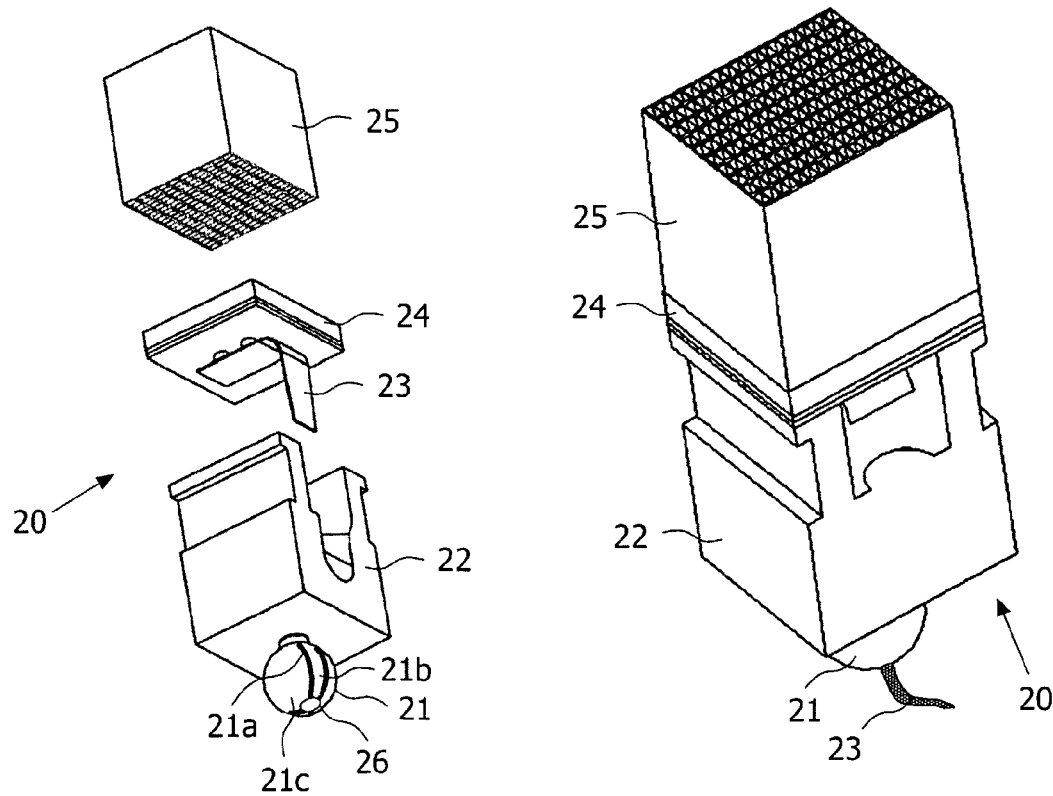
FIG.2
FIG.3

MODULAR DEVICE FOR THE DETECTION AND/OR TRANSMISSION OF RADIATION WITH SELF-ALIGNING MODULES

The invention relates to a modular device for the detection and/or transmission of radiation with a carrier and a set of modules, a carrier for a such a device, a module for such a device, and an imaging device with such a device.

In the U.S. Pat. No. 5,991,357 an X-ray detector for a CT (computed tomography) system is described which comprises an annular carrier and a set of detector modules that are disposed on the carrier in one line. The detector modules comprise a housing with two holes for fixing them to the carrier by means of pins or bolts. The construction of larger, especially two-dimensional arrays of detector modules is not intended and not possible with the system described in this document.

Based on this situation it was an object of the present invention to provide a modular device, for example a radiation detector, that can easily be assembled in a large variety of dimensions and/or shapes.

This object is achieved by a modular device according to claim 1, a carrier according to claim 13, a module according to claim 14, and an imaging device according to claim 15. Preferred embodiments are disclosed in the dependent claims.

The modular device according to the present invention may be a detector or a transmitter for any kind of radiation including electromagnetic radiation, especially X-rays, and (ultra-)sound. In the following a detector for radiation will often be considered as an example for the device though the invention is not restricted to such an application. The modular device comprises the following components:

A carrier with a mounting surface and a set of first connecting elements.

A set of modules for detecting incident radiation or for transmitting radiation, wherein each of the modules comprises a second connecting element that can be coupled to one of the first connecting elements to form a joint (i.e. a coupling that allows a limited relative movement between the connecting elements).

Said modular device has the advantage that an array of modules can readily be assembled by coupling the modules to corresponding first connecting elements on the mounting surface of the carrier. The shape of the mounting surface can for example be chosen such that a desired shape of the sensitive area of a radiation detector results. Moreover, the individual modules can easily be aligned in a desired direction, for example the focus of an X-ray tube in a CT-system, because they are coupled to the carrier by joints.

The joints formed by the connecting elements are preferably swivel joints, i.e. joints that allow rotation on at least one axis and/or revolution around a point. Alternatively, the joints may be linear joints that allow a linear relative movement between the connecting elements.

According to a preferred embodiment of the modular device, the modules may come into contact with each other when they are mounted on the carrier. Due to these contacts, the modules exert forces on each other, wherein the sum of all forces (or, more precisely, the potential energy) will be minimized by corresponding displacements of the detector modules that are allowed due to the flexible coupling to the carrier. In this way, the detector modules of the radiation detector become self-aligning. In the final state, however, there is ideally (if all tolerances are kept) no contact but a small gap between the modules.

According to a preferred embodiment, the modules comprise a mechanically robust base portion that is larger in diameter than other parts of the module. Contacts between the modules are therefore made via the base portions, thereby protecting sensitive parts of the module.

The first and second connecting elements of the carrier and modules, respectively, can in principle be realized in many different ways. According to a first embodiment, the second connecting elements are balls or cylinders which allow a rotational movement about a point or an axis, respectively, when coupled to a corresponding bearing.

According to a second embodiment, the first connecting elements may particularly be constituted by circular or rectangular holes in the mounting surface, wherein the second connecting elements can be snapped into or through said holes or fixed to the holes by a locking element (e.g. a screw or a nut). An advantage of this embodiment is that the holes can readily be produced by drilling of a carrier which may for example be a metal sheet with a certain shape. The first and second embodiments may especially be combined. Thus, a ball/cylinder as second connecting element may for example be snapped into a circular/rectangular hole or engaged through said hole. In order to allow a snap-mechanism, the diameter of the balls/cylinders should be slightly greater than the diameter of the entrance to the holes, and the material of the carrier and/or of the balls/cylinders should be somewhat elastic. In such a case the first and second connecting elements form a ball-and-socket joint or a hinge, respectively, which can easily be assembled and disassembled. The balls/cylinders are typically located on the underside of the modules, such that the modules themselves can be arranged close to each other in order to constitute a practically gapless sensitive area of the detector.

In a further development of the second embodiment described above, the second connecting elements (e.g. balls or cylinders) protrude from the backside of the carrier when they are fixed to the holes of the carrier. Thus the second connecting elements are easily accessible from the backside of the carrier, from where they may be pushed back in order to remove a module from the carrier. The disassembling of a module can thus be performed without any special tools.

According to a third embodiment, the second connecting elements may be flexible rods, for example tightly wound spirals. Such rods will allow a movement of the module on (approximately) a spherical surface around the fixing point of the rods on the carrier.

The mounting surface may be of any shape that is required for a given application. Particularly, the mounting surface may be a part of a plane, a cylinder or a sphere. In case of a cylinder or a sphere, the modules will become aligned to the axis of the cylinder or the centre of the sphere, respectively. Such an arrangement is for example needed in X-ray devices where the X-ray tube is located at the centre of the sphere.

The detector modules may principally be of any shape and dimension. Preferably, the detector modules have a shape that allows the gapless filling of a plane. Particularly they may be formed like prisms with a rectangular cross section (i.e. they are blocks or cuboids) or like prisms with a hexagonal cross section, such that they can be arranged in a regular grid to cover a certain area without any gaps in between.

According to a preferred embodiment of the invention, the modules comprise a sensitive unit for the detection of incident radiation and an anti-scatter grid that is disposed on said unit. The anti-scatter grid may be made for example from a moldable material like a polymer by injection molding or from metal by casting. Its purpose is to prevent the arrival of scattered radiation on the sensitive units, thus improving the signal-to-noise ratio. Moreover, such modules may comprise a scintillator for the conversion of X-rays into optical photons.

In most cases it will be required to contact the modules electrically, for example in order to supply an operating voltage, to control them or to read signals from them. To provide at least some of these electrical connections, the first and second connecting elements are preferably adapted to make at least one electrical contact when coupled together. Most preferably they are adapted to make two contacts for the supply of an operating voltage via the carrier.

The invention further comprises a carrier and a module for a modular device of the kind described above. These components may have any of the features that were mentioned above with respect to the whole modular device.

Moreover, the invention comprises an imaging device that contains an X-ray sensitive modular device of the kind described above. This imaging device may particularly be a CT-system or a PET (Positron Emission Tomography) scanner.

These and other aspects of the invention will be apparent from and elucidated with reference to the embodiment(s) described hereinafter.

In the following the invention is described by way of example with the help of the accompanying drawings in which:

FIG. 1 is a perspective view of a partially assembled radiation detector according to the present invention;

FIG. 2 is an exploded view of a detector module according to the present invention;

FIG. 3 is a perspective view of the assembled module of FIG. 2.

The example that is shown in the Figures refers to a detector for an X-ray device like a CT-system, though the invention is not restricted to this application. Regarding X-ray devices, there is a need for detectors that can in principle be arbitrarily extended in the longitudinal direction of a patient (Z-direction). This requirement may be fulfilled by the radiation detector that is described in the following.

According to FIG. 1, the radiation detector 1 comprises a carrier 10 and a set of detector modules 20 that are arranged on the carrier 10 in a regular pattern. The carrier or vat 10 has the shape of a rectangular section from a sphere and may be made of a metal sheet. Moreover, the carrier 10 has an array of through holes 11 that are arranged in a rectangular grid. The axes of these holes 11 are aligned towards the centre of the sphere that describes the shape of the carrier 10. During the use of the radiation detector 1, the focus of the X-ray beam is located at said centre of the sphere.

In FIG. 1, the radiation device 1 is shown in a partially assembled state, i.e. some of the holes 11 are not equipped with sensor modules 20, and some of the sensor modules 20 do not carry an anti-scatter grid. The construction of the sensor modules 20 will now be described in more detail with reference to FIGS. 2 and 3.

Each sensor module 20 comprises mainly three components, namely

A base portion 22. The base portion 22 is preferably mechanically robust, e.g. made from a solid material, and larger in diameter than the rest of the module in order to protect sensitive parts of the module from contacting each other. Moreover, the base portion 22 comprises empty spaces for the accommodation of electronic components and/or for the establishment of channels through which cables may be laid.

A sensitive unit 24 that is adapted to detect incident X-radiation and to convert it into an electric signal which may be read out from outside via an electrical connector 23. Typically the sensor unit 24 comprises a scintillator to convert X-rays into optical photons and an array of photo sensors to register said photons.

An anti-scatter grid 25 that is located above the sensor unit 24.

The anti-scatter grid 25 is a single channel shielding grid which may for example be produced by injection molding using a moldable material in which X-ray absorbing materials are embedded. Alternatively, the anti-scatter grid 25 may be produced by casting of X-ray absorbing alloys.

FIG. 3 shows the detector unit 20 in its assembled state. In a mounting process the alignment between the anti-scatter grid 25 and the scintillator of the sensor unit 24 is performed while stacking the grid 25 onto the scintillator 24. Anti-scatter grid 25 and sensor unit 24 are then affixed to the base portion 22. The whole module has in principle the shape of a block or cuboid, wherein the sensitive unit 24 and the anti-scatter grid 25 extend in all directions to the borders of the body (apart from the small oversize of the base portion 22 mentioned above). Thus, the sensor modules 20 can be put adjacent to each other practically without any gap between them, thus forming a continuous sensitive detector area.

The base portion 22 has on its underside a ball 21 on a small neck. The dimension of this ball 21 is such that it fits into the holes 11 of the carrier 10 that were described above. Therefore, the sensor modules 20 can be fixed to the mounting surface 12 of the carrier 10, wherein the holes 11 and the balls 21 together form ball-and-socket joints that allow rotational movement of the sensor module 20 within a certain interval. The balls 21 may be fixed to the holes 11 by a snap mechanism or simply by fitting. Moreover, they might be fixed by an additional locking element, e.g. by a screw from the backside of the carrier 10 or by a threaded bushing and a nut that press the ball towards the carrier 10. Of course connecting elements with other geometrical forms could be used instead of the balls 21, e.g. open balls, cylinders, (flexible) rods or the like.

When all a sensor modules 20 are mounted in their respective holes 11, their mutual contact leads to a self-alignment of all modules. Thus a regular geometrical structure results by self-organization and without the need of laborious alignment processes. A further fixation of the detector modules 20 is not necessary, in particular if the radiation detector 1 is used in an CT-system where it usually rotates at high speed which keeps the modules 20 in place by centrifugal forces.

Another advantage of the described design is that the balls 21 extend through the holes 11 and protrude somewhat from the backside of the carrier 10. Therefore, a user may easily push a module out of its hole 11 without any tools if that module shall be removed, for example in order to replace it by a new one.

The contacting of the sensor modules 20 for control purposes and signal readout can be provided in different ways. In the embodiment of FIGS. 2 and 3, the ball 21 contains a hole 26 through which a flexible electrical cable 23 or optical fiber may run to the backside of the carrier 10. Cables or fibers might also be led through channels that are established by recesses and/or holes of the base portion 22. Moreover, the side faces of the modules 20 might contain optical transmitters and receivers (not shown) for the exchange of data by optical signals.

As can be seen in FIG. 2, the ball 21 (or any other connecting element) can be subdivided into two or more contact zones 21c that are separated by isolators 21a and preferably also intermediate separating zones 21b. When mounted to the carrier 10, the contact zones 21c touch corresponding contact zones on the carrier. These contacts may then be used in order to supply an operating voltage to the modules 20.

The design principle of the detector module 1 may be used in any situation where large areas of modules shall be assembled. This may particularly be the case in connection with CT-systems or PET scanners.

Finally it is pointed out that in the present application the term "comprising" does not exclude other elements or steps, that "a" or "an" does not exclude a plurality, and that a single processor or other unit may fulfill the functions of several means. Moreover, reference signs in the claims shall not be construed as limiting their scope.

The invention claimed is:

1. A modular device for the detection and/or transmission of radiation, comprising:
    a carrier with a mounting surface and a set of first connecting elements; and
    a set of modules for the detection and/or transmission of radiation, each of said modules comprising a second connecting element that is capable of being coupled to one of said first connecting elements to form a joint;
    wherein said joint is adapted to allow rotation of each module relative to the carrier and to allow said set of modules to self-align by mutually contacting each other.

2. The modular device according to claim 1, wherein the joint is adapted to allow rotation on at least one axis and/or revolution around a point.

3. The modular device according to claim 1, wherein the modules comprise a base portion that is larger in diameter than other parts of the module.

4. The modular device according to claim 1, wherein the second connecting elements are balls or cylinders.

5. The modular device according to claim 1, wherein the first connecting elements are circular or rectangular holes in the mounting surface and the second connecting elements are capable of being snapped into or through said holes or fixed to the holes by a locking element.

6. The modular device according to claim 5, wherein the second connecting elements protrude from the backside of the carrier when fixed to the holes.

7. The modular device according to claim 1, wherein the second connecting elements are flexible rods.

8. The modular device according to claim 1, wherein the mounting surface is a section of a plane, a cylinder or a sphere.

9. The modular device according to claim 1, wherein the modules have a shape that allows the gapless filling of a plane, particularly the shape of a prism with a rectangular or hexagonal cross section.

10. The modular device according to claim 1, wherein the modules comprise a sensitive unit on which an anti-scatter grid is mounted.

11. The modular device according to claim 1, wherein the first and second connecting elements are adapted to make at least one electrical contact when coupled together.

12. An imaging device, particularly a CT-system or a PET scanner, comprising an X-ray sensitive modular device according to claim 1.

13. A carrier for a modular device for the detection and/or transmission of radiation, comprising:
    a mounting surface; and
    a set of first connecting elements that are capable of being coupled with second connecting elements of modules to form a joint;
    wherein said joint is adapted to allow rotation of each module relative to the mounting surface and to allow said modules to self-align by mutually contacting each other.

14. A module for a modular device for the detection and/or transmission of radiation, comprising:
    a second connecting element that is capable of being coupled to a first connecting element of a carrier to form a joint;
    wherein said joint is adapted to allow rotation of each module relative to the carrier and to allow a set of said modules to self-align by mutually contacting each other.

15. A modular device for the detection and/or transmission of radiation, comprising:
    a carrier with a mounting surface;
    a set of holes formed in the mounting surface; and
    a set of modules for the detection and/or transmission of radiation, each of said modules comprising a ball configured for inserting into one of said holes to form a joint.

16. The modular device of claim 15, wherein said joint is adapted to allow rotation of each module relative to the mounting surface and to allow said modules to self align by mutually contacting each other.

17. The modular device according to claim 15, wherein the joint is adapted to allow rotation on at least one axis and/or revolution around a point.

18. The modular device according to claim 15, wherein said holes are circular holes in the mounting surface and the balls of the modules are capable of being snapped into or through said holes or fixed to the holes by a locking element.

19. The modular device according to claim 15, wherein said holes are rectangular holes in the mounting surface and the balls of the modules are capable of being snapped into or through said holes or fixed to the holes by a locking element.

* * * * *